United States Patent
He et al.

(10) Patent No.: US 9,078,577 B2
(45) Date of Patent: Jul. 14, 2015

(54) CIRCUIT FOR HEARTBEAT DETECTION AND BEAT TIMING EXTRACTION

(71) Applicant: Massachusetts Institute of Technology, Cambridge, MA (US)

(72) Inventors: David Da He, Cambridge, MA (US); Charles G. Sodini, Belmont, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 13/798,440

(22) Filed: Mar. 13, 2013

(65) Prior Publication Data

US 2014/0163386 A1 Jun. 12, 2014

Related U.S. Application Data

(60) Provisional application No. 61/734,064, filed on Dec. 6, 2012.

(51) Int. Cl.
*A61B 5/04* (2006.01)
*A61B 5/024* (2006.01)
(Continued)

(52) U.S. Cl.
CPC ............. *A61B 5/04017* (2013.01); *A61B 5/024* (2013.01); *A61B 5/0245* (2013.01); *A61B 5/0255* (2013.01); *A61B 5/02416* (2013.01); *A61B 5/02438* (2013.01);
(Continued)

(58) Field of Classification Search
USPC ........................................ 600/508–509, 521
See application file for complete search history.

(56) References Cited

U.S. PATENT DOCUMENTS 3,590,811 A 7/1971 Harris
4,240,442 A 12/1980 Andresen et al.
(Continued)

FOREIGN PATENT DOCUMENTS

EP 0003567 10/1984
EP 0262779 4/1988
(Continued)

OTHER PUBLICATIONS

Han, Hyonyoung et al.: "Development of a Wearable Health Monitoring Device with Motion Artifact Reduced Algorithm (ICCAS 2007)", International Conference on Control, Automation and Systems 2007, pp. 1581-1584, Oct. 17-20, 2009, Seoul, Korea.
(Continued)

Primary Examiner — Paula J Stice
(74) Attorney, Agent, or Firm — K&L Gates LLP

(57) ABSTRACT

A circuit and method for long term electrocardiogram (ECG) monitoring is implemented with the goal of reducing power consumption, battery size, and consequently device size. In one embodiment, the integrated circuit includes an amplifier cell having a plurality of input terminals and an output terminal; a QRS amplifier cell in communication with the output of the amplifier cell; a baseline amplifier cell in communication with the output of the amplifier cell; a comparator cell having a first input terminal in communication with the output terminal of the QRS amplifier cell; and a $V_{DC}$ cell having an input in communication with the output of the baseline amplifier cell and an output in communication with the second input terminal of the comparator cell, wherein the comparator cell generates an output pulse in response to the output signal from the amplifier cell and the output signal from the baseline amplifier cell.

16 Claims, 15 Drawing Sheets

(51) Int. Cl.

| | |
|---|---|
| A61B 5/0245 | (2006.01) |
| A61B 5/0456 | (2006.01) |
| A61B 5/08 | (2006.01) |
| A61B 5/11 | (2006.01) |
| A61B 5/00 | (2006.01) |
| H03K 6/02 | (2006.01) |
| A61B 5/0255 | (2006.01) |
| A61B 5/0428 | (2006.01) |
| A61B 5/0452 | (2006.01) |
| A61B 5/0432 | (2006.01) |

(52) U.S. Cl.
CPC ............ *A61B 5/0428* (2013.01); *A61B 5/0452* (2013.01); *A61B 5/0456* (2013.01); *A61B 5/08* (2013.01); *A61B 5/1102* (2013.01); *A61B 5/72* (2013.01); *A61B 5/7203* (2013.01); *A61B 5/7207* (2013.01); *H03K 6/02* (2013.01); *A61B 5/0432* (2013.01); *A61B 5/0816* (2013.01)

(56) References Cited

U.S. PATENT DOCUMENTS

| | | | |
|---|---|---|---|
| 4,854,699 | A | 8/1989 | Edgar, Jr. |
| 7,479,111 | B2 | 1/2009 | Zhang et al. |
| 7,751,872 | B2 | 7/2010 | Clayman |
| 7,769,435 | B2 | 8/2010 | Kuo et al. |
| 7,846,104 | B2 | 12/2010 | MacQuarrie et al. |
| 8,157,730 | B2 | 4/2012 | LeBoeuf et al. |
| 2003/0045787 | A1 | 3/2003 | Schulze et al. |
| 2003/0080963 | A1 | 5/2003 | Van Hook et al. |
| 2005/0101872 | A1 | 5/2005 | Sattler et al. |
| 2005/0209516 | A1 | 9/2005 | Fraden |
| 2005/0235092 | A1 | 10/2005 | Ballew et al. |
| 2007/0032731 | A1 | 2/2007 | Lovejoy et al. |
| 2007/0197881 | A1 | 8/2007 | Wolf et al. |
| 2008/0139955 | A1 | 6/2008 | Hansmann et al. |
| 2009/0167771 | A1 | 7/2009 | Franko et al. |
| 2010/0016694 | A1 | 1/2010 | Martin et al. |
| 2010/0094147 | A1 | 4/2010 | Inan et al. |
| 2010/0113948 | A1 | 5/2010 | Yang et al. |
| 2010/0153592 | A1 | 6/2010 | Freimuth et al. |
| 2010/0256460 | A1 | 10/2010 | Haveri et al. |
| 2010/0298660 | A1 | 11/2010 | McCombie et al. |
| 2011/0066042 | A1 | 3/2011 | Pandia |
| 2011/0219208 | A1 | 9/2011 | Asaad et al. |
| 2011/0252260 | A1 | 10/2011 | Flachs et al. |
| 2011/0302357 | A1 | 12/2011 | Sullivan |
| 2012/0005539 | A1 | 1/2012 | Paul et al. |
| 2012/0203077 | A1 | 8/2012 | He et al. |

FOREIGN PATENT DOCUMENTS

| | | |
|---|---|---|
| EP | 1072284 | 1/2001 |
| EP | 1774907 | 4/2007 |
| EP | 2116183 | 11/2009 |
| GB | 2408105 | 5/2005 |
| WO | 03088841 A2 | 10/2003 |
| WO | 2008058328 | 5/2008 |
| WO | 2008095318 | 8/2008 |
| WO | 2010025166 A1 | 3/2010 |
| WO | 2010108287 | 9/2010 |
| WO | 2011113070 A1 | 9/2011 |
| WO | 2013130317 | 9/2013 |
| WO | 2013192166 | 12/2013 |

OTHER PUBLICATIONS

Pinheiro, Eduardo et al.: "Pulse Arrival Time and Ballistocardiogram Application to Blood Pressure Variability Estimation", MeMeA—International Workshop on Medical Measurements and Applications, pp. 132-136, May 29-30, 2009, Cetraro, Italy.

Pinheiro, Eduardo et al.: "Theory and Developments in an Unobtrusive Cardiovascular System Representation: Ballistocardiography", The Open Biomedical Engineering Journal, pp. 201-216, vol. 4, 2010.

van Brummelen, A.G.W. et al.: "On the Elimination of Pulse Wave Velocity in Stroke Volume Determination from the Ultralow-Frequency Displacement Ballistocardiogram", Fysisch Laboratorium, pp. 374-378, May 6, 1963, Utrecht, Netherlands.

Johnson, James, Project Leader: "15607—A Wearable Vital Signs Monitor for Single Site, Cuff-Less Blood Pressure Measurements", Research Report, 46 pp., Research Report No. 11359131-1, May 29, 2012.

International Search Report of the International Searching Authority for International Patent Application No. PCT/U2013/046293 issued on Oct. 11, 2013 (4 pgs.).

Chen et al., "Development of a Portable EEG Monitoring System based on WLAN," Proceedings of the 2007 IEEE International Conference on Networking, Sensing and Control, London, UK, Apr. 15-17, 2007, pp. 460-465.

Chung et al., "Development of a Heart Rate Monitor Based on an Ear Phone," World Congress on Medical Physics and Biomedical Engineering, Sep. 7-12, 2009, Munich, Germany, IFMBE Proceedings vol. 25/12, 2009, pp. 423-425.

Guo et al., "A Long-term Wearable Vital Signs Monitoring System Using BSN," IEEE Computer Society, 11th Euromicro Conference on Digital System Design Architectures Methods and Tools, Mar. 30, 2010, pp. 825-830.

He et al., "The Ear as a Location for Wearable Vital Signs Monitoring," 32nd Annual International Conference of the IEEE EMBS, Buenos Aires, Argentina, Aug. 31-Sep. 4, 2010, pp. 6389-6392.

Hejjel et al., "The corner frequencies of the ECG amplifier for heart rate variability analysis," Institute of Physics Publishing, Physiol. Meas. 26, 2005, pp. 39-47.

Inan et al., "Non-invasive Measurement of Valsalva-induced Hemodynamic Changes on a Bathroom Scale Ballistocardiograph," 30th Annual International IEEE EMBS Conference, Vancouver, British Columbia, Canada, Aug. 20-24, 2008, pp. 674-677.

Inan et al., "Robust ballistocardiogram acquisition for home monitoring," Institute of Physics Publishing, Physiol. Meas. 30 (2009) pp. 169-185.

Keselbrener et al., "Nonlinear high pass filter for R-wave detection in ECG signal," Med. Eng. Phys., vol. 19, No. 5, pp. 481-484, 1997, published by Elsevier Science Ltd.

Kim et al., "A New Method for Unconstrained Pulse Arrival Time (PAT) Measurement on a Chair," J. Biomed. Eng. Res. vol. 27, Jun. 2006, pp. 83-88.

Poon et al., "Cuff-less and Noninvasive Measurements of Arterial Blood Pressure by Pulse Transit Time," Proceedings of the 2005 IEEE, Engineering in Medicine and Biology 27th Annual Conference, Shanghai, China, Sep. 1-4, 2005, pp. 5877-5880.

Shin et al., "Non-constrained monitoring of systolic blood pressure on a weighing scale," Physiol. Meas. 30, 2009, pp. 679-693.

Tabakov et al., "Online Digital Filter and QRS Detector Applicable in Low Resource ECG Monitoring Systems," Annals of Biomedical Engineering, vol. 36, No. 11, Nov. 2008, pp. 1805-1815.

Tavakoli et al., "An Ultra-Low-Power Pulse Oximeter Implemented With and Energy-Efficient Transimpedance Amplifier," IEEE Transactions on Biomedical Circuits and Systems, vol. 4, No. 1, Feb. 2010, pp. 27-38.

Wang et al., "Multichannel Reflective PPG Earpiece Sensor With Passive Motion Cancellation, IEEE Transactions on Biomedical Circuits and Systems," vol. 1, No. 4, Dec. 2007, pp. 235-241.

Yoo et al., "An 8-Channel Scalable EEG Acquisition SoC with Fully Integrated Patient-Specific Seizure Classification and Recording Processor," IEEE International Solid-State Circuits Conference, 2012, pp. 3-5.

Zhang et al., "A Low-Power ECoG/EEG Processing IC with Integrated Multiband Energy Extractor," IEEE Transactions on Circuits and Systems—I: Regular Papers, vol. 58, No. 9, Sep. 2011, pp. 2069-2082.

Zhang et al., "Design on Sampling Circuit of EEG Signal Based on AT89C2051 Single-chip," IEEE Fourth International Conference on Innovative Computing, Information and Control, 2009, pp. 454-457.

http://www.esa.int/SPECIALS/TTP2/SEM48O1PLFG_0.html, Oct. 25, 2010, 2 pages.

(56) References Cited

OTHER PUBLICATIONS http://www.economist.com/node/17416748?story_id=17416748, Nov. 4, 2010, 2 pages.

http://www.csem.ch/site/card.asp?bBut=yes&pld=4293, printed on Dec. 24, 2010, 3 pages.

International Search Report for PCT International Application No. PCT/US2013/026839, mailed Apr. 29, 2013, 1 page.

PCT International Search Report and Written Opinion of International Searching Authority for International Patent Application No. PCT/US2011/041446, mailed May 23, 2012, 32 pages.

PCT International Preliminary Report on Patentability and Written Opinion for International Patent Application No. PCT/US2011/041446, mailed Aug. 13, 2013, 23 pages.

PCT International Search Report and Written Opinion of International Searching Authority for International Patent Application No. PCT/US2013/046293, mailed Oct. 11, 2013, 16 pages.

PCT International Search Report and Written Opinion of International Searching Authority for International Patent Application No. PCT/US2013/073538, mailed Mar. 14, 2014, 15 pages.

Harrison, Reid et al.: "A Low-Power Low-Noise CMOS Amplifier for Neural Recording Applications," IEEE Journal of Solid-State Circuits, Jun. 2003, vol. 38, No. 6, pp. 958-965.

Kim, Hyejung et al.: "A Configurable and Low-Power Mixed Signal SoC for Portable ECG Monitoring Applications," Symposium on VLSI Circuits Digest of Technical Papers, 2011, 14-1, pp. 142-143.

Jocke, S.C. et al.: "A 2.6μW Sub-threshold Mixed-signal ECG SoC," Symposium on VLSI Circuits Digest of Technical Papers, 2009, 6-2, pp. 60-61.

Mandal, Soumyajit et al.: "Fast Startup CMOS Current References," Circuits and Systems, 2006, ISCAS 2006 Proceedings, 2006 IEEE International Symposium on, May 2006, pp. 2845-2848.

Miyahara, Masaya et al.: "A Low-Noise Self-Calibrating Dynamic Comparator for High-Speed ADCs," IEEE Asian Solid-State Circuits of Conference, Nov. 3-5, 2008, Fukuoka, Japan, pp. 269-272.

Yazicioglu, Refet Firat et al.: "A 30μW Analog Signal Processor ASIC for Biomedical Signal Monitoring," IEEE International Solid-State Circuits Conference, 2010, ISSCC 2010, Session 6, Displays & Biomedical Devices, 6.6, pp. 124-126.

Daly, Denis C., et al.: "A 6-bit, 0.2 V to 0.9 V Highly Digital Flash ADC with Comparator Redundancy," IEEE Journal of Solid-State Circuits, Nov. 2009, vol. 44, No. 11, pp. 3030-3038.

PCT International Preliminary Report on Patentability, Application No. PCT/US2013/046293, mailed Dec. 31, 2014, 12 pages.

110

| Subject | Number of Beats | Mean R-wave Timing Error [ms] | Stdev. R-wave Timing Error [ms] | Sampling Freq. [Hz] |
|---|---|---|---|---|
| 1 | 250 | 0.91 | 1.6 | 250 |
| 2 | 183 | 0.91 | 1.6 | 250 |
| 3 | 63 | 0.97 | 2.2 | 250 |
| 4 | 123 | -1.70 | 1.6 | 250 |
| 5 | 73 | -2.40 | 1.8 | 250 |
| 6 | 467 | -1.50 | 0.71 | 500 |
| 7 | 363 | -1.00 | 0.71 | 500 |
| 8 | 357 | -2.80 | 0.72 | 500 |
| 9 | 226 | -0.88 | 0.72 | 500 |
| 10 | 199 | -0.29 | 0.84 | 500 |
| Overall | 2,304 | -0.70 | 1.25 | - |

Fig. 17

CIRCUIT FOR HEARTBEAT DETECTION AND BEAT TIMING EXTRACTION

RELATED APPLICATIONS

This application claims priority to U.S. Provisional Application 61/734,064 filed Dec. 6, 2012, the entire contents of which are herein incorporated by reference.

FIELD OF THE INVENTION

This invention relates generally to heartbeat monitors and more specifically to portable, wearable heartbeat monitors.

BACKGROUND OF THE INVENTION

Referring to FIG. 1, traditionally the circuit topology for heartbeat detection circuit 10 known to the prior art consists of a low noise instrumentation amplifier (IA) 14, an anti-alias filter 18, an analog-to-digital converter (ADC) 22, and a digital signal processor (DSP) or microcontroller 26. This topology is generally employed in a wearable clinical heart monitor.

In this topology, the IA 14 amplifies the differential Electrocardiogram (ECG) signal derived from patient electrodes, using low noise operational amplifiers (op-amps) to minimize the addition of circuit noise. The gain of the IA 14 is set so that the amplified output is not saturated. The output signal from the IA next passes through the anti-alias filter 18, and then the ADC 22 uniformly quantizes the ECG signal, treating small features such as ECG's P wave and large features such as ECG's R wave with equal resolution. The ADC 22 is usually implemented with a medium resolution successive approximation register (SAR) architecture to minimize power consumption. Finally, to detect heartbeats, the digitized ECG is processed by the microprocessor 26 using a peak detection algorithm to detect R-waves. Depending on the computational power of the available microprocessor or DSP 26, such an algorithm ranges from a simple thresholding algorithm to one employing wavelet transforms.

This traditional topology is necessary for clinical ECG measurements, where multilead or multielectrode ECG signals are acquired with high quality in order to diagnose complex arrhythmias. These recordings are usually quantized with at least 12 bits to preserve the finer details of the P wave of the ECG. The American Heart Association recommends that the ADC use a sampling frequency of at least 150 Hz to capture all features, while stating that a bandwidth of 1 Hz to 30 Hz generally produces a stable ECG without digitization artifacts.

However, for applications employing the wearable heart monitor, generally only the R-wave timing is relevant. What is needed is a monitor that will provide this timing while removing the need for ADC and signal processing and thereby significantly decreasing the circuit's power requirements and size while robustly extracting heartbeat timings in the presence of motion artifacts and degraded signal quality.

The present invention addresses this need using a new topology for the heartbeat detection circuit.

SUMMARY OF THE INVENTION

In one aspect, the invention relates to an integrated circuit for heartbeat detection. In one embodiment, the integrated circuit includes an amplifier cell, such as a PGA amplifier cell, having a plurality of input terminals and an output terminal; a QRS amplifier cell having an input terminal and an output terminal, the input terminal of the QRS amplifier cell in communication with the output terminal of the amplifier cell; a baseline amplifier cell having an input terminal and an output terminal, the input terminal of the baseline amplifier cell in communication with the output terminal of the amplifier cell; a comparator cell having a first input terminal and a second input terminal and an output terminal, the first input terminal of the comparator cell in communication with the output terminal of the QRS amplifier cell; and a $V_{DC}$ cell having a first input terminal in communication with the output terminal of the baseline amplifier cell and an output terminal in communication with the second input terminal of the comparator cell, wherein the amplifier cell outputs an output signal on the output terminal of the amplifier cell in response to input signals input to the input terminals of the amplifier cell, and wherein the comparator cell generates an output pulse in response to the output signal from the QRS amplifier cell and the output signal from the $V_{DC}$ cell.

In another embodiment, the $V_{DC}$ cell has a second input terminal, and the integrated circuit further includes a microcontroller cell having an input terminal in communication with the output terminal of the comparator cell and an output terminal in communication with the second input terminal of the $V_{DC}$ cell.

In another aspect, the invention relates to a method for detecting a heartbeat. In one embodiment, the method includes the steps of amplifying a signal from an ECG electrode to form an amplified ECG signal; amplifying the amplified ECG signal with an amplifier having a bandwidth of 20-40 Hz to form a QRS signal; amplifying the amplified ECG signal with an amplifier having a bandwidth of 1 Hz to generate baseline voltage; adding a DC offset to the baseline to form an offset baseline; comparing the QRS signal to the offset baseline; and generating an output signal if the QRS signal is greater than the offset baseline. In another embodiment, the method further includes adjusting the amplification value of the ECG electrode signal. In yet another embodiment, the timing of an R-wave is estimated in response to measuring the midpoint timing of its corresponding digital output pulse.

In yet another aspect, the invention relates to a method of selecting a DC offset. In one embodiment, the method includes the steps of (a.) setting a DC voltage to a predetermined value; (b.) comparing an amplified filtered ECG signal to the sum of a baseline signal and DC voltage to produce an output signal; (c.) if the output signal is not a series of regularly spaced pulses of 40 ppm to 180 ppm then incrementing the DC voltage; (d.) iteratively repeating steps b and c until the output signal is a series of regularly spaced pulses of 40 ppm to 180 ppm.; and (e.) setting the DC offset at the value of the DC voltage.

In still yet another aspect, the invention relates to a method of selecting an offset baseline. In one embodiment, the method includes the steps of (a.) determining the peak voltage of an R-wave of a heartbeat; (b.) determining a baseline DC voltage; and (c.) calculating one-half the difference between the baseline DC voltage and peak voltage of the heartbeat and adding the baseline DC voltage to obtain the offset baseline.

In another aspect, the invention relates to a detection device that, in one embodiment, includes an amplifier cell having a plurality of input terminals and an output terminal; a signal amplifier cell having an input terminal and an output terminal, the input terminal of the signal amplifier cell in communication with the output terminal of the amplifier cell; a baseline amplifier cell having an input terminal and an output terminal, the input terminal of the baseline amplifier cell in communication with the output terminal of the amplifier cell; a comparator cell having a first input terminal and a second input terminal and an output terminal, the first input terminal of the comparator cell in communication with the output terminal of the signal amplifier cell; and a $V_{DC}$ cell having a first terminal in communication with the output terminal of the baseline amplifier cell and a second terminal in communication with the second input terminal of the comparator cell, wherein the amplifier cell outputs an output signal on the output terminal of the amplifier cell in response to input signals input to the input terminals of the amplifier module, and wherein the comparator cell generates an output pulse in response to the output signal from the signal amplifier cell and the output signal from the $V_{DC}$ cell. In another embodiment, the signal at the input of the amplifier is one of a PPG, a BCG and a respiration signal.

In yet another aspect, the invention relates to a method for detecting a periodic signal comprising the steps of amplifying a signal from a signal source to form an amplified signal; amplifying the amplified signal with an amplifier having a bandwidth of sufficient to form a filtered amplified signal with the highest frequency pulsatile features of amplified signal preserved; amplifying the amplified signal with an amplifier having a bandwidth sufficient to preserve the baseline while removing the pulsatile components; adding a DC offset to the baseline to form an offset baseline; comparing the filtered amplified signal to the offset baseline; and generating an output signal if the filtered amplified signal is greater than the offset baseline. In one embodiment, the bandwidth of the baseline is 1 Hz. In another embodiment, the bandwidth of the baseline is 0.05 Hz.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

FIG. 3(c) is an embodiment of a digital output corresponding to the waveforms in FIG. 3(a) and measured by the system of FIG. 2 when the baseline is raised to b2 in FIG. 3a;

FIG. 12(a) is a chest ECG taken with a subject at rest (gain=52 dB);

FIG. 12(b) is the output signal of the device of FIG. 3 of the ECG of FIG. 12a;

FIG. 17 is a table of R-wave timing as estimated from the midpoint timing of $D_{out}$ pulses.

DESCRIPTION OF A PREFERRED EMBODIMENT

The proposed new circuit topology is based on the fact that heartbeat detection relies on QRS complex of the ECG, which has a higher frequency content and a greater magnitude than adjacent ECG features. A generalized embodiment of this circuit topology 40 is shown in FIG. 2, along with a general illustration of the ECG waveform (FIG. 3(a)) and the output of the circuit (FIG. 3(b and c)).

Figure 1:
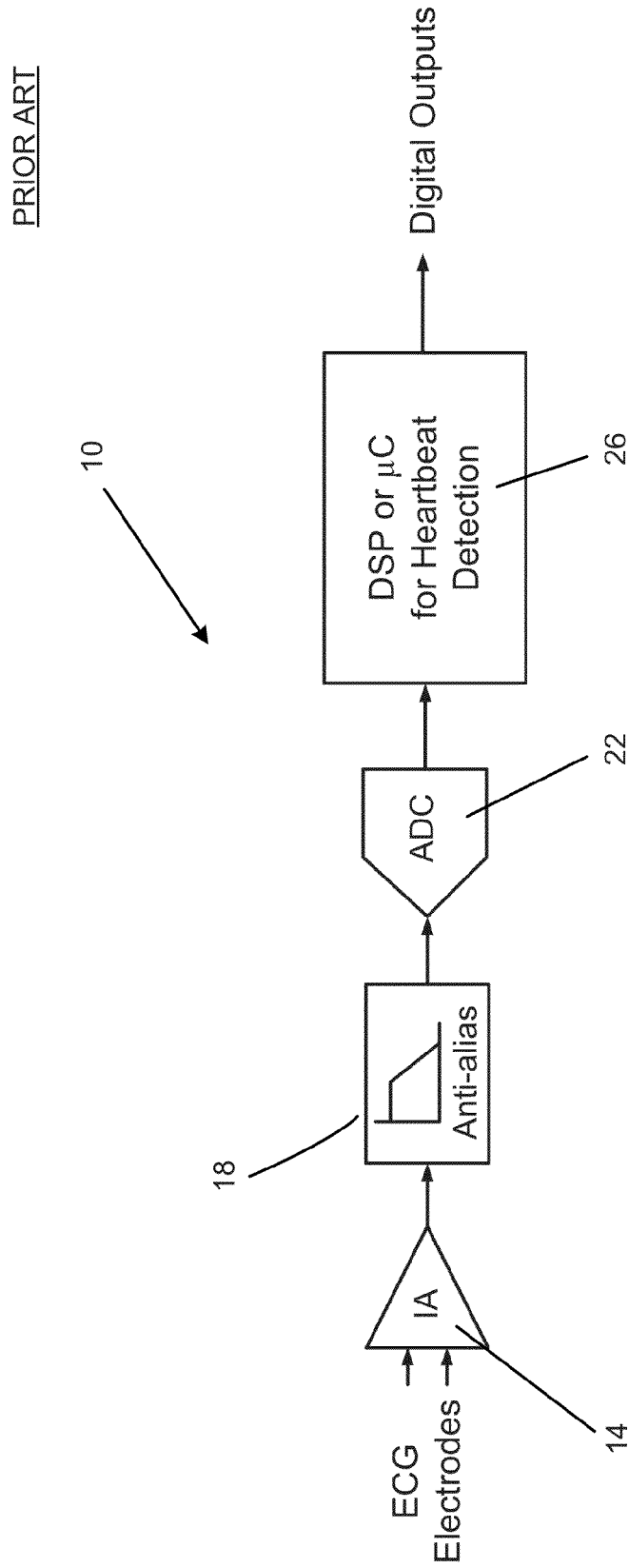
FIG. 1 is a standard topology of a heartbeat detection circuit known to the prior art.
Figure 2:
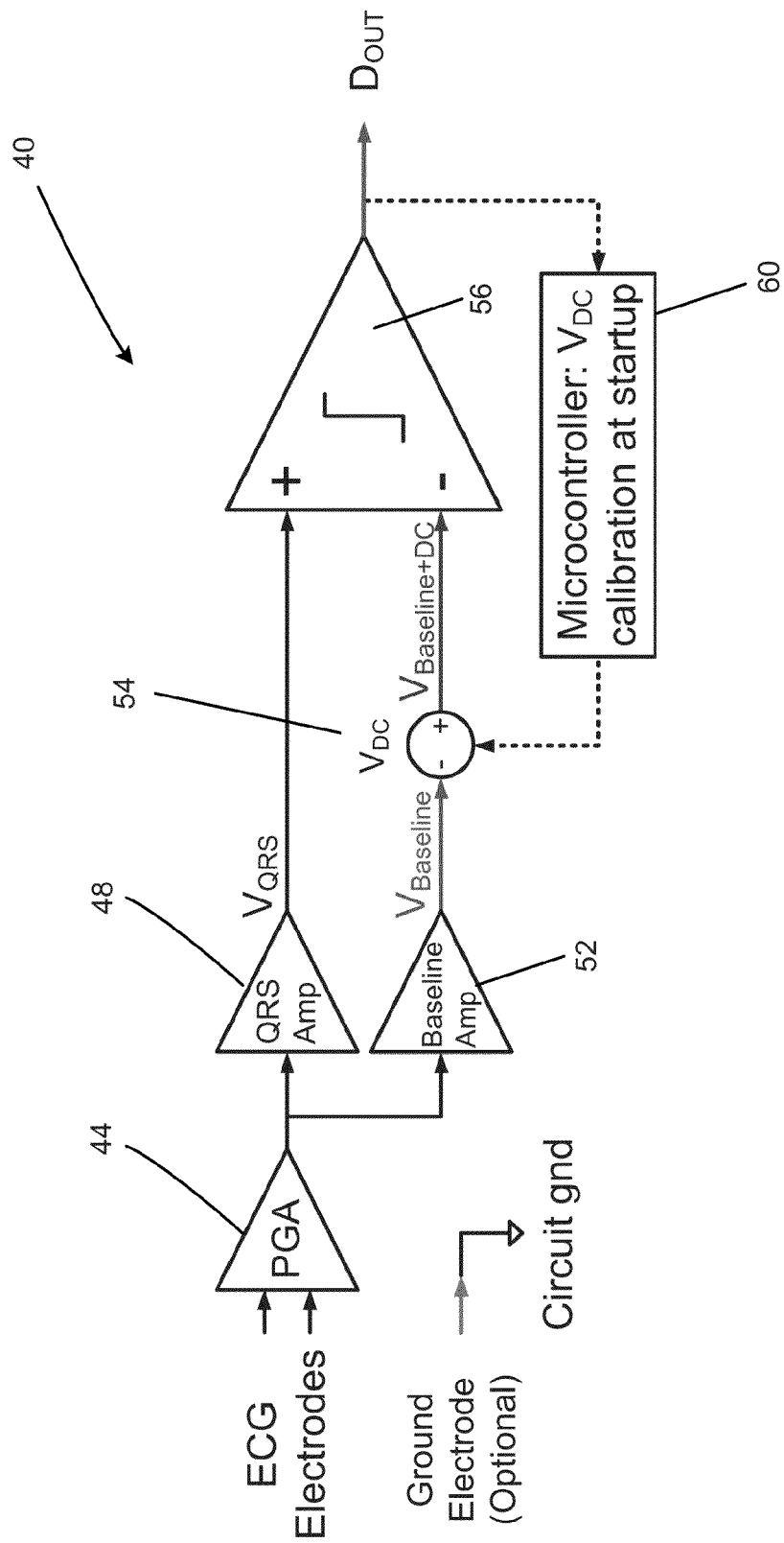
FIG. 2 is an embodiment of a new topology for ECG heartbeat detection with voltage nodes labeled as constructed in accordance with the invention.

In FIG. 2, a differential ECG signal is first amplified by a low noise gain amplifier 44. In one embodiment, the gain amplifier is a programmable gain amplifier, or PGA. The output signal of the amplifier 44 is split into two paths. The first signal path is to an amplifier termed a "QRS Amp" 48, which has a bandwidth of 20 Hz to 40 Hz that preserves the signal structure of the QRS complex. The second signal path is to an amplifier termed a "Baseline Amp" 52, which is a low pass filter amplifier with an equal gain but a lower bandwidth than the QRS Amp 48. This Baseline Aamp 52, which has a bandwidth of about 1 Hz, preserves only the low frequency baseline drift in the ECG signal caused by motion artifacts. If respiration is the signal, then a bandwidth of about 0.05 is used to remove the respiration signals from baseline A positive inline DC offset $V_{DC}$ 54 is added to the output ($V_{Baseline}$) of the Baseline Amp 52 to create an adaptive threshold signal equal to ($V_{Baseline+DC}$) using a $V_{DC}$ circuit described in detail below. Using this threshold value, a QRS complex (or heartbeat) is detected whenever $V_{QRS} > V_{Baseline+DC}$. In this circuit, this comparison is performed by a comparator 56, which consequently pulses a high output signal ($D_{OUT}$) when a heartbeat is detected.

Figure 3A:
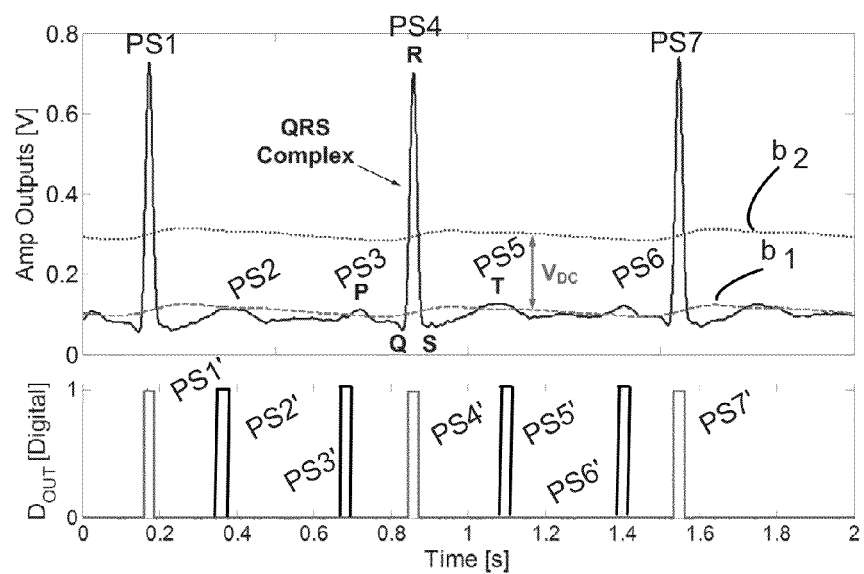
FIG. 3(a) is a series of matched time waveforms illustrating the QRS complex, baseline, and $V_{Baseline}$ with $V_{DC}$ offset.
Figure 3B:
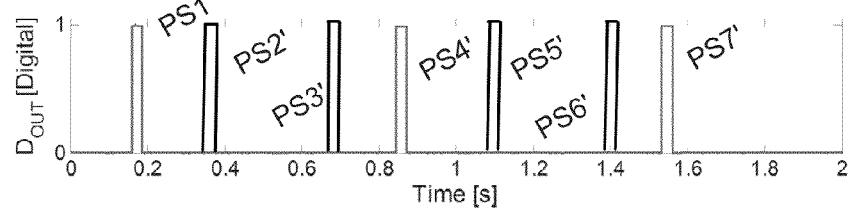
FIG. 3(b) is an embodiment of a digital output corresponding to the waveforms in FIG. 3(a) and measured by the system of FIG. 2 when the baseline is set at b1.
Figure 3C:
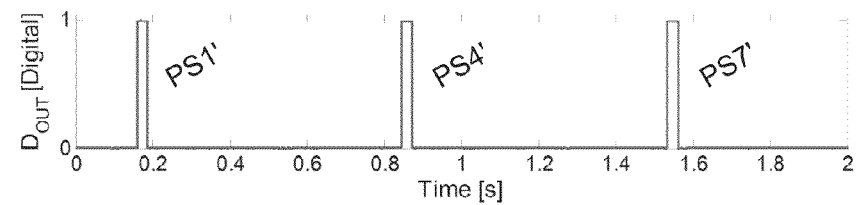

To correctly set the DC offset voltage ($V_{DC}$), the DC offset voltage is incremented until the period between $D_{OUT}$ pulses is regular and is in the range of human beat-to-beat interval. As shown in FIG. 3(a), there is a wide range of valid $V_{DC}$ values since $V_{DC}$ can be set at any signal voltage level between the R-wave voltage level and the voltage level of the next highest feature (usually the T-wave). Referring to FIGS. 3(a) and 3(b), with the baseline originally set at (b1) (shown here at about 0.1V), multiple peaks (ps1-ps7) in the signal(s) (FIG. 3(a)) would generate pulses (ps1'-ps7') at the output $D_{OUT}$ of the circuit (FIG. 3(b)). These pulses are irregular in time and would not be considered to correspond to a series of heartbeat pulses. Next, the $V_{DC}$ voltage value is iteratively increased and fewer and fewer peaks in the signal(s) trigger the output signal pulses. These step increases continue until at some value (b2) (FIG. 3(a)), the output signal $D_{OUT}$ is reduced to a regular time series of pulses (ps1, ps4, ps7) as shown in FIG. 3(c).

This $V_{DC}$ voltage value is set initially by an off chip microcontroller 60 (FIG. 2) at the beginning of measurement, and the calibration routine generally takes less than one minute. The external microcontroller 60 then is powered off after the calibration is complete, or until the time series of the pulses at the output $D_{OUT}$ become irregular again and a recalibration has to be done. The pulses can become irregular for multiple reasons such as a change in position of the patient, as shown in the ECGs below. The microprocessor 60 includes configuration registers to load 77 bits of configuration settings into the ASIC using shift registers. The shift registers are modified to be able to serially read out internal bits for verification. The configuration settings include: $C_{Gnd}$ settings (7 bits), $C_{VDD}$ settings (4 bits), and reverse $V_{DC}$ (1 bit).

Figure 4A:
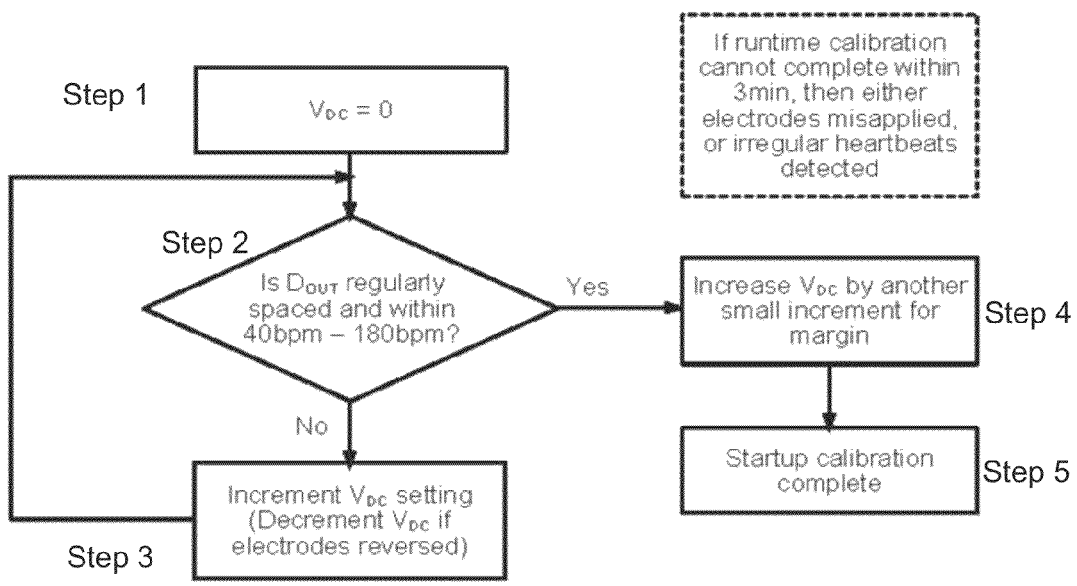
FIGS. 4(a) and 4(b) are flow charts of embodiments of the calibration of the system at startup (4(a)) and runtime (4(b)) accomplished by raising the baseline.

Referring to FIG. 4(a), during initial setup, the microprocessor 60 sets $V_{DC}$=0 (Step 1). The output $D_{OUT}$ is checked to determine if the pulses of $D_{OUT}$ are both regularly spaced and within the range of 40-180 pulses per minute (ppm) (Step 2). If not, $V_{DC}$ is incremented (or decremented if the electrodes are reversed) (Step 3) and the output $D_{OUT}$ is checked to determine if the pulses of $D_{OUT}$ are both regularly spaced and within the range of 40-180 pulses per minute (ppm) (Step 2) again. These steps are repeated until the pulses of $D_{OUT}$ are both regularly spaced and within the range of 40-180 pulses per minute (ppm). At this point, $V_{DC}$ is incremented slightly as a safety margin (Step 4) and calibration is complete (Step 5). The pulses per minute (ppm) now correspond to the beats per minute (bpm).

Figure 4B:
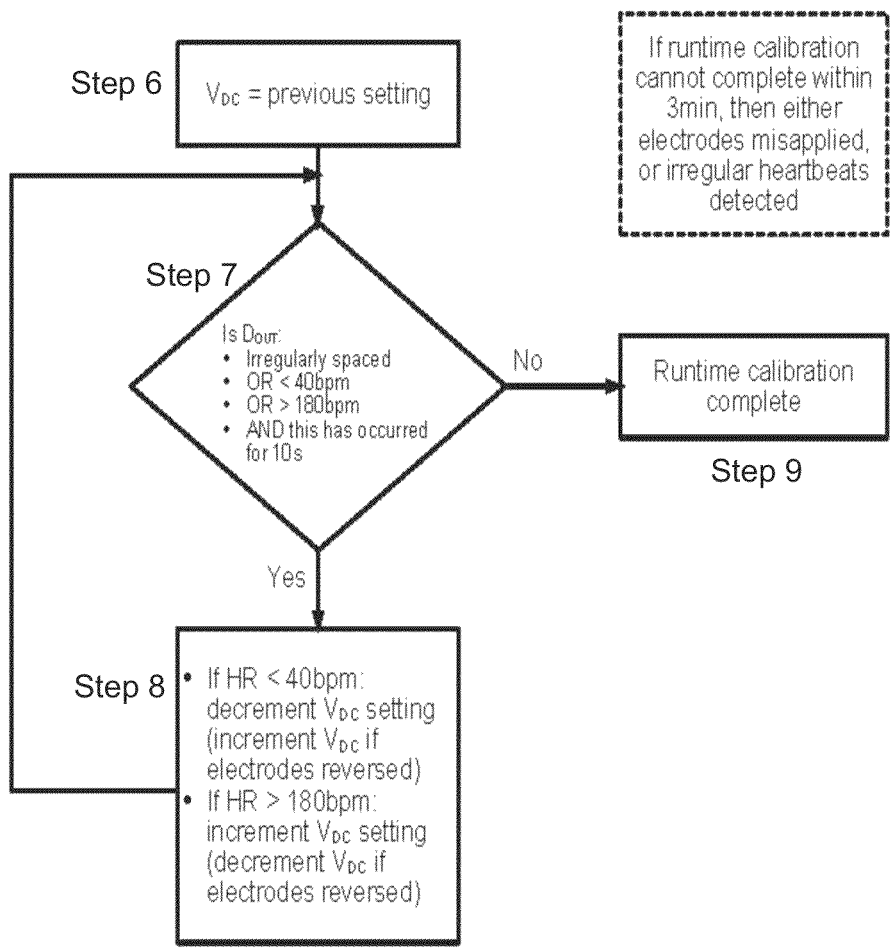

Referring to FIG. 4(b), at runtime, the microprocessor 60 sets $V_{DC}$ equal to the previous value set during calibration (Step 6). The output $D_{OUT}$ is checked to determine if the pulses of $D_{OUT}$ are irregularly spaced, or outside the range of 40-180 pulses per minute (ppm), and have been so for ten seconds (Step 7). If yes, then if the pulses are less than 40 per minute, $V_{DC}$ is decremented (or incremented if the electrodes are reversed) (Step 8). If the pulses are greater than 180 per minute, $V_{DC}$ is incremented (or decremented if the electrodes are reversed) (also Step 8). In both cases, the output $D_{OUT}$ is checked to determine if the pulses of $D_{OUT}$ are irregularly spaced and outside the range of 40-180 pulses per minute (ppm) and have been so for ten seconds (Step 7) again. These steps are repeated until the pulses of $D_{OUT}$ are both regularly spaced and within the range of 40-180 beats per minute (ppm). At this point, $V_{DC}$ calibration is complete (Step 9).

Alternatively, the above method of setting $V_{DC}$ can be accelerated if the R-wave peak voltage level is known in advance, in which case $V_{DC}$ initially can be set at the midpoint between a baseline near zero and R-wave peak voltage. This measurement avoids the region of $V_{DC}$ where $V_{Baseline+DC}$ is close to $V_{Baseline}$ and thus $D_{OUT}$ is noisy and invalid.

Figure 5:
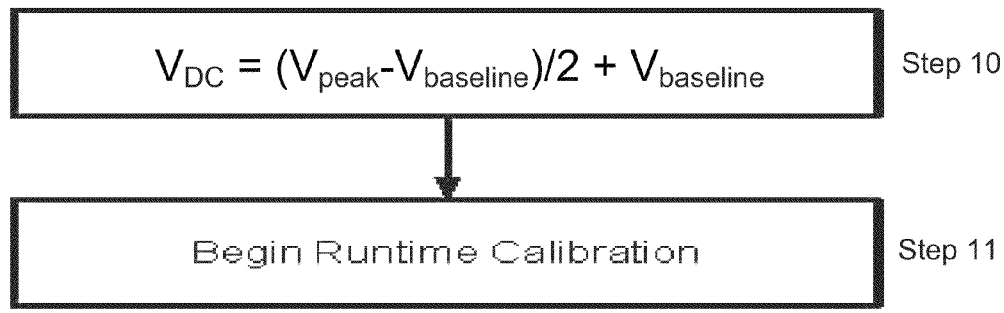
FIG. 5 is a flowchart of an embodiment of the calibration of the system using the accelerated process.

Referring to FIG. 5, the flowchart of the accelerated calibration described above is shown. In (Step 10) the value of $V_{DC}$ is set as one-half the difference between the peak voltage and the baseline voltage, and this result added to the baseline voltage:

$$V_{DC}=(V_{peak}-V_{baseline})/2+V_{baseline} \quad (1)$$

At this point, the calibration is complete (Step 11).

There are several advantages to this new topology in terms of circuit design. First, no signal processor or ADC is required, which significantly further reduces the device power consumption and physical die area. Second, a low voltage supply is possible because a clipped R-wave that exceeds the amplifier's dynamic range still possesses beat information. Third, any comparator offset is automatically compensated for due to the $V_{DC}$ calibration. Fourth, amplifier linearity is unimportant because the signal path is highly nonlinear. In terms of practical usage, this topology is tolerant to motion artifacts because the signal is compared against its own baseline. Furthermore, no predefined subject-dependent parameters are needed.

The function of the $V_{DC}$ generator 54 (FIG. 6) is to provide a voltage $V_{DC}$ to add to $V_{Baseline}$ to produce an adaptive threshold $V_{Baseline+DC}$. The schematic of an embodiment of the $V_{DC}$ generator 54 is shown in FIG. 7.

In more detail, $C_{VDD}$ is a 4-bit binary weighted capacitor bank of capacitors ranging from 15 fF to 155 fF, and $C_{Gnd}$ is a 7-bit binary weighted capacitor bank of capacitors ranging from 40 fF to 5.1 pF. The $C_{VDD}$ and $C_{Gnd}$ values that are to be used are selected during the initial $V_{DC}$ calibration by the microcontroller 60 (FIG. 2).

Figure 6:
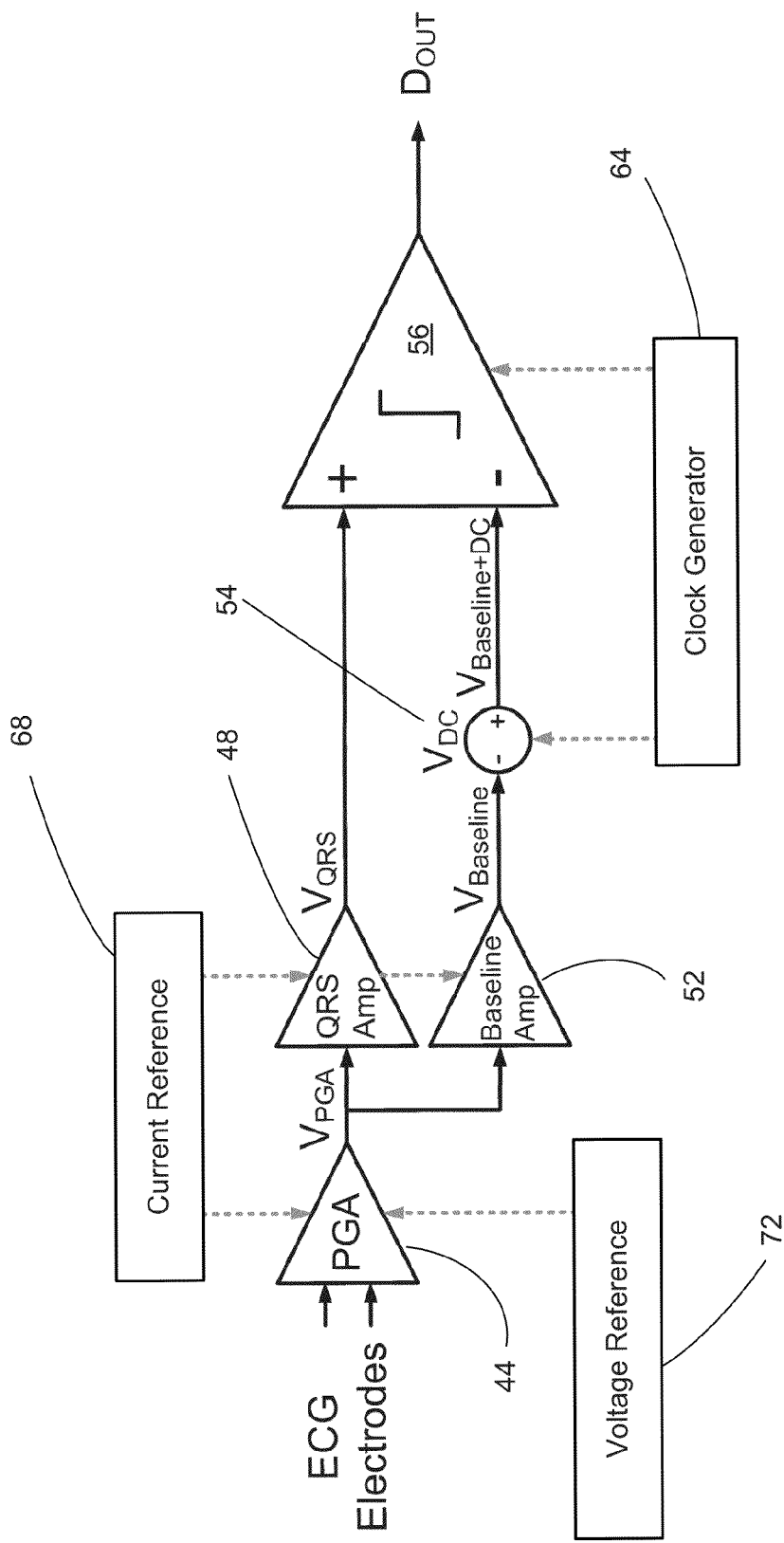
FIG. 6 is a block diagram of an embodiment of the circuit components for an ECG ASIC, constructed in accordance with the invention.
Figure 7:
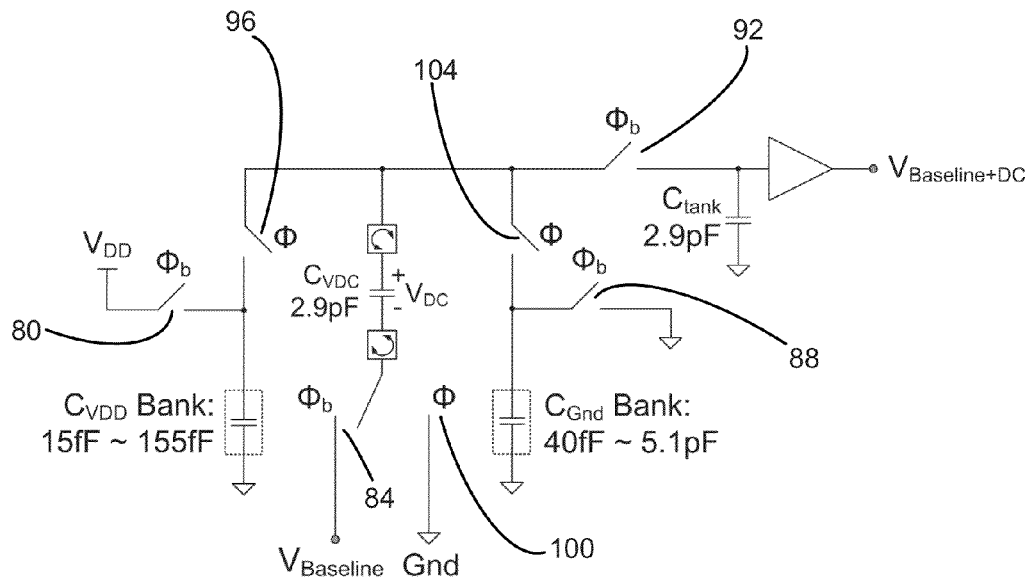
FIG. 7 is a schematic diagram of an embodiment of a $V_{DC}$ generator constructed in accordance with the invention.
Figure 8A:
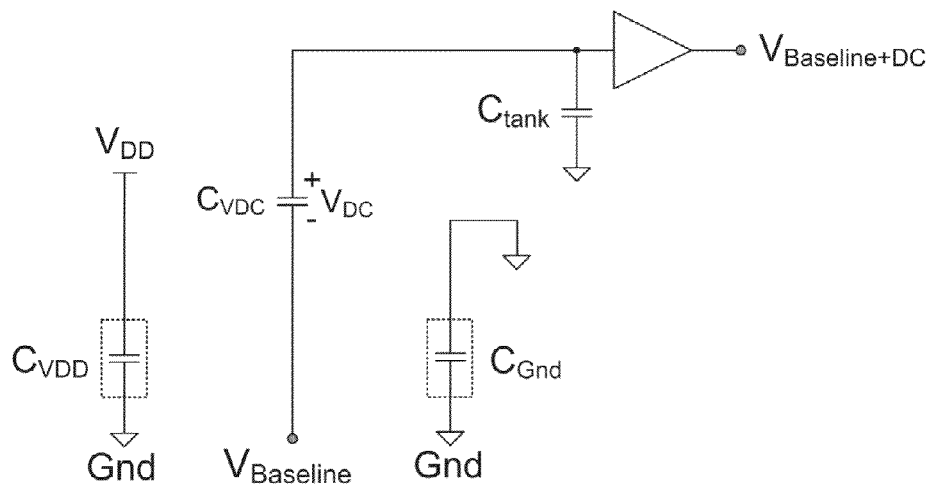
FIG. 8(a) is a diagram of the operation of the $V_{DC}$ generator of FIG. 7 during clock phase $\Phi_b$.
Figure 8B:
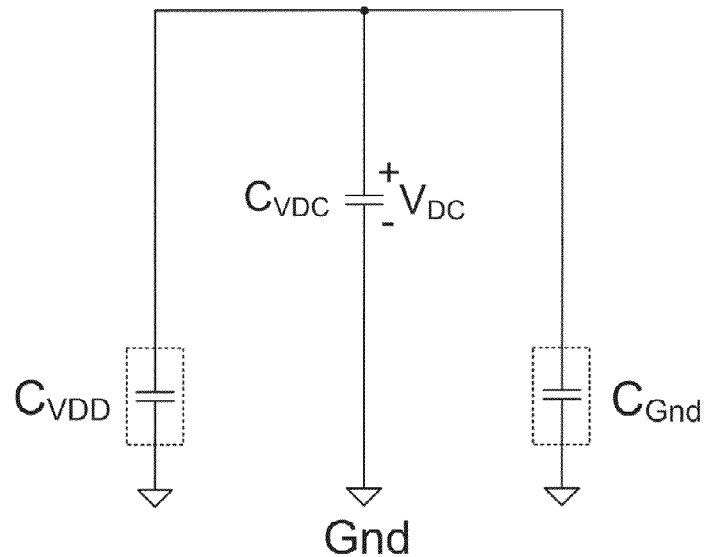
FIG. 8(b) is a diagram of the operation of the $V_{DC}$ generator of FIG. 7 during clock phase $\Phi$.

Non-overlapping clock phases $\Phi$ and $\Phi_b$ are generated on-chip at 1.9 kHz by the clock generator 64 (FIG. 6). The clock frequency is chosen as a compromise between low power (which favors lower frequency) and low charge leakage (which favors higher frequency). During clock phase $\Phi_b$ (FIG. 7 and FIG. 8a), capacitor banks $C_{VDD}$ and $C_{Gnd}$ are reset to $V_{DD}$ and ground respectively by closing switches 80, 84, 88 and 92 and the opening of switches 96, 100 and 104. During the following clock phase 1 (FIG. 7 and FIG. 8b), capacitor $C_{VDC}$ is charged to a final voltage of $V_{DC}=V_{DD}C_{VDD}/(C_{VDD}+C_{Gnd})$. During this clock phase $\Phi$ (FIG. 8b), switches 80, 84, 88 and 92 are opened and switches 96, 100 and 104 are closed. $V_{DC}$ is added to $V_{Baseline}$ to produce $V_{Baseline+DC}$, while $C_{VDD}$ and $C_{Gnd}$ are again reset. Capacitor $C_{tank}$ is present to reduce voltage ripples.

Figure 9:
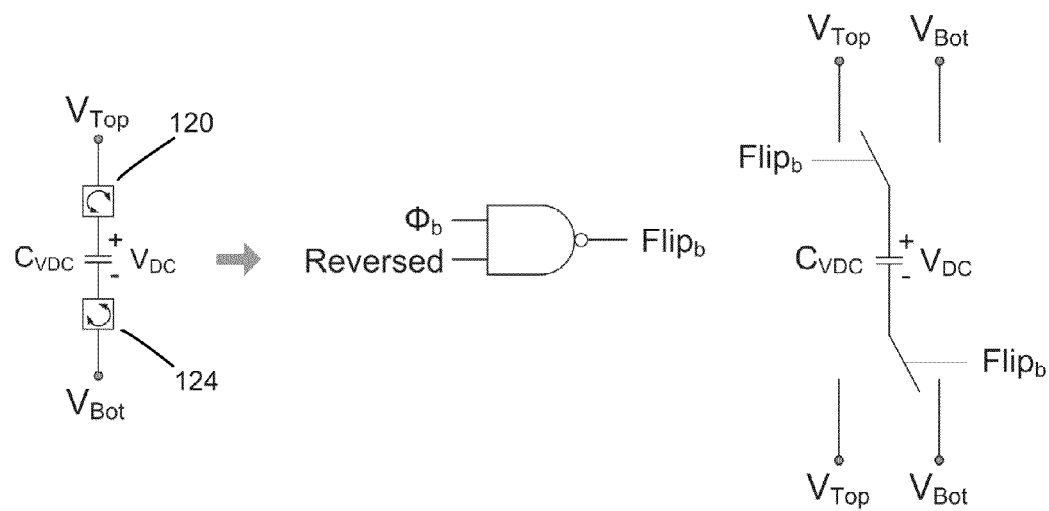
FIG. 9 is a diagram of the switch configurations of a portion of the $V_{DC}$ generator of FIG. 7 showing that the sign of $C_{VDC}$ can be flipped during phase $\Phi_b$ in case of reversed electrodes.

In consideration of potential long term at-home usage where the ECG electrodes are applied by the wearer, the $V_{DC}$ generator has the ability to generate negative $V_{DC}$ if the user accidentally reverses the electrodes. This is symbolized by the two digital blocks 120, 124 in FIG. 7 and FIG. 9 that can reverse $C_{VDC}$ during phase $\Phi_b$. In this case, where the ECG polarity is reversed and $C_{VDC}$ is reversed, then the heartbeat occurs when $D_{OUT}=0$ instead of $D_{OUT}=1$.

The role of the comparator 56 is to output a digital high (or digital low if electrodes are reversed) when a QRS complex has occurred, that is, when $V_{QRS}>V_{Baseline+DC}$. A dynamic latched comparator is used in one embodiment. The dynamic topology is chosen because it consumes power only when latching.

Figure 10:
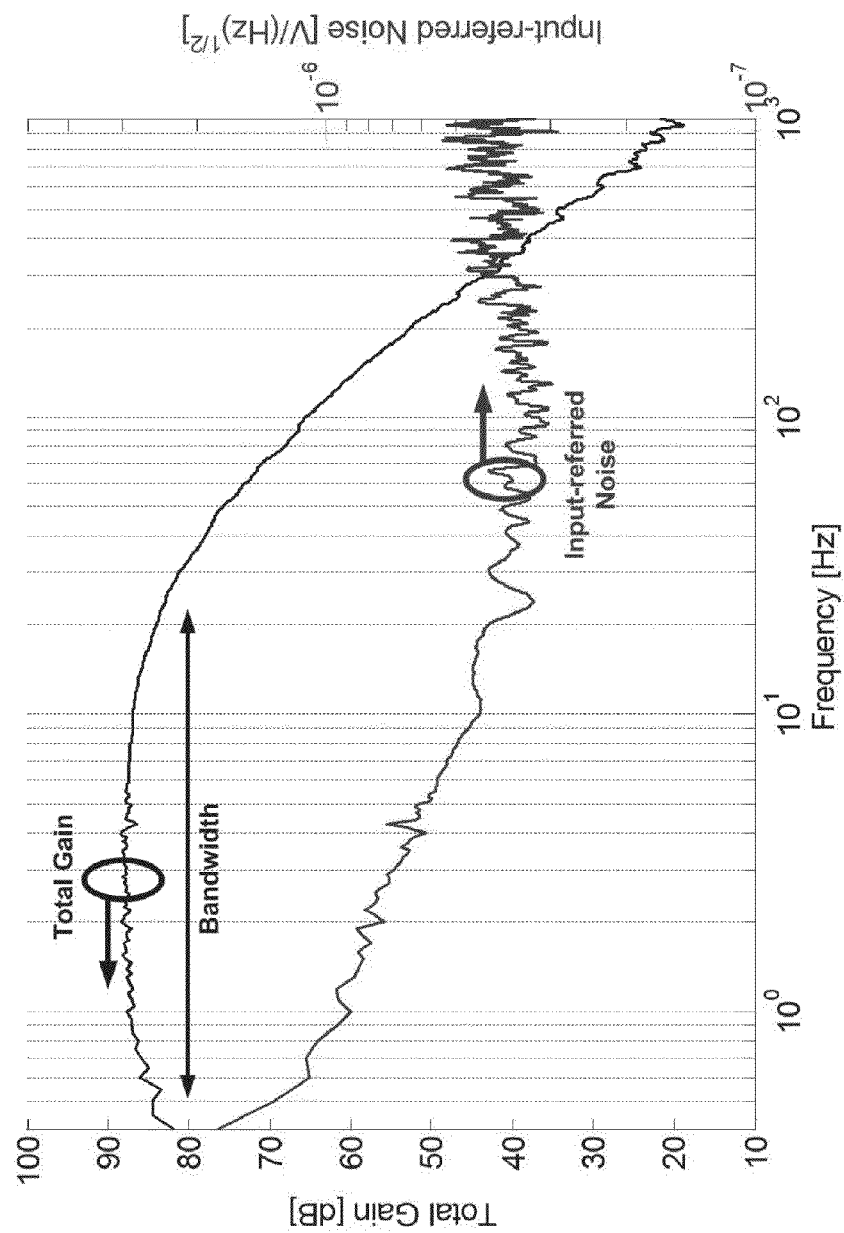
FIG. 10 is graph of gain response and noise response of an embodiment of a PGA-QRS Amp signal path measured using an Agilent 35670A Dynamic Signal Analyzer.

The ECG's amplification path goes through the amplifier and then QRS Amp. FIG. 10 shows the gain response and input-referred noise response at the highest gain setting in an embodiment using a PGA amplifier. The measured level of noise is compatible with sensing ECG at the head, where the QRS amplitude is approximately 30 $\mu V_{pp}$.

A widely used figure of merit for amplifier power-noise performance is the Noise Efficiency Factor (NEF) which is defined as:

$$NEF = V_{ni,rms}\sqrt{\frac{2I_{total}}{\pi V_{thermal} 4kTBW}} \quad (2)$$

Figure 11:
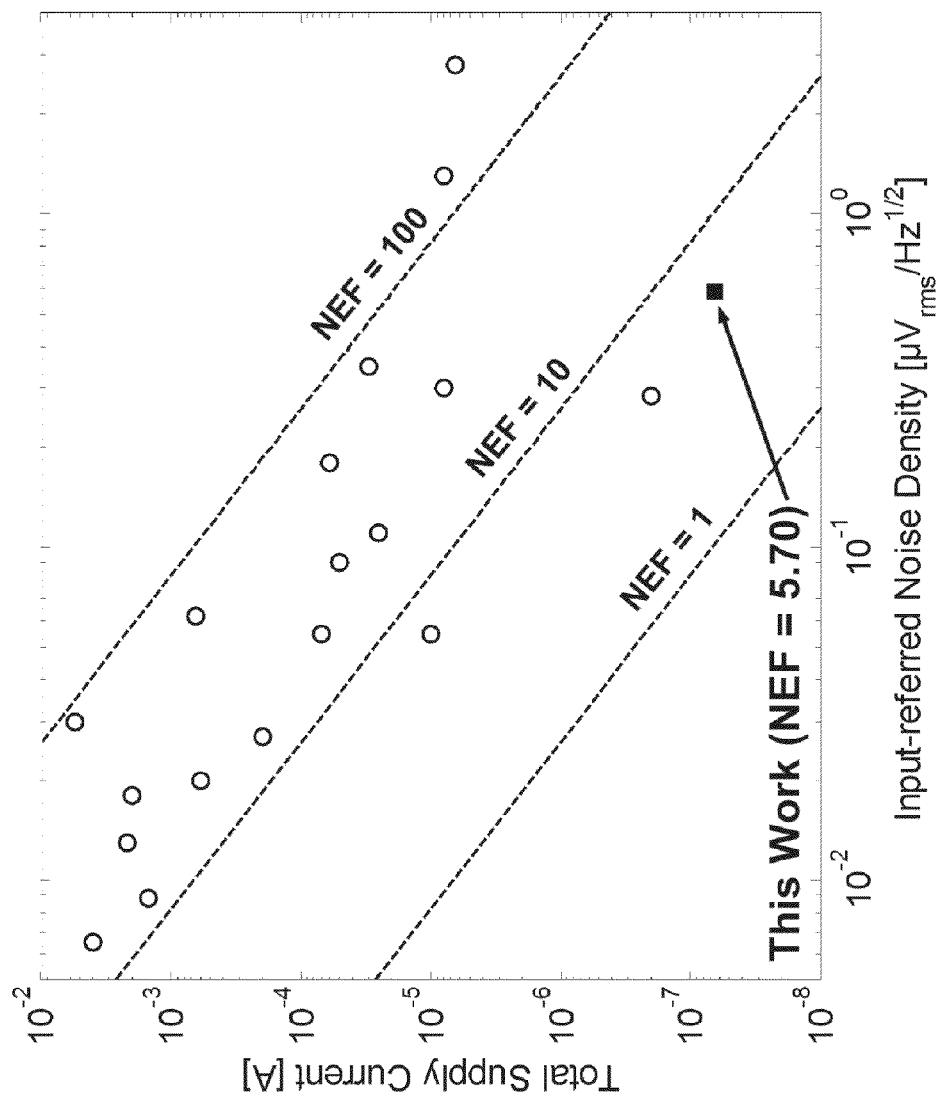
FIG. 11 is a comparison graph of an embodiment of the PGA-QRS Amp's Noise efficiency Factor (NEF) plotted against other published biopotential amplifiers.

In Equation (2), $V_{ni,rms}$ is the input-referred RMS noise voltage, $I_{total}$ is the total amplifier supply current, and BW is the amplifier bandwidth in Hertz. T is the absolute temperature and $V_{thermal}$ is equal to kT/q where q is the charge on the electron and k is the Boltzmann constant. This value is about 25 mV at room temperature. The NEF for the PGA-QRS Amp circuit blocks is 5.7. FIG. 11 compares the ECG ASIC's amplifier performance with published biopotential front-end amplifiers, where it is the lowest powered amplifier with an NEF of less than 10.

Figure 12:
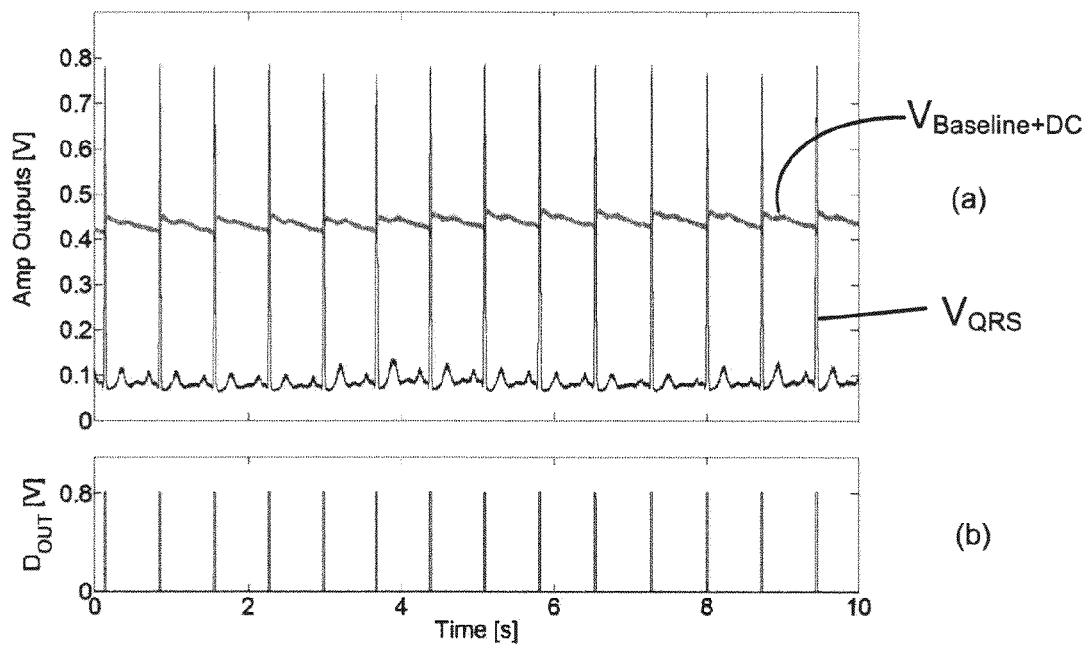
Figure 13:
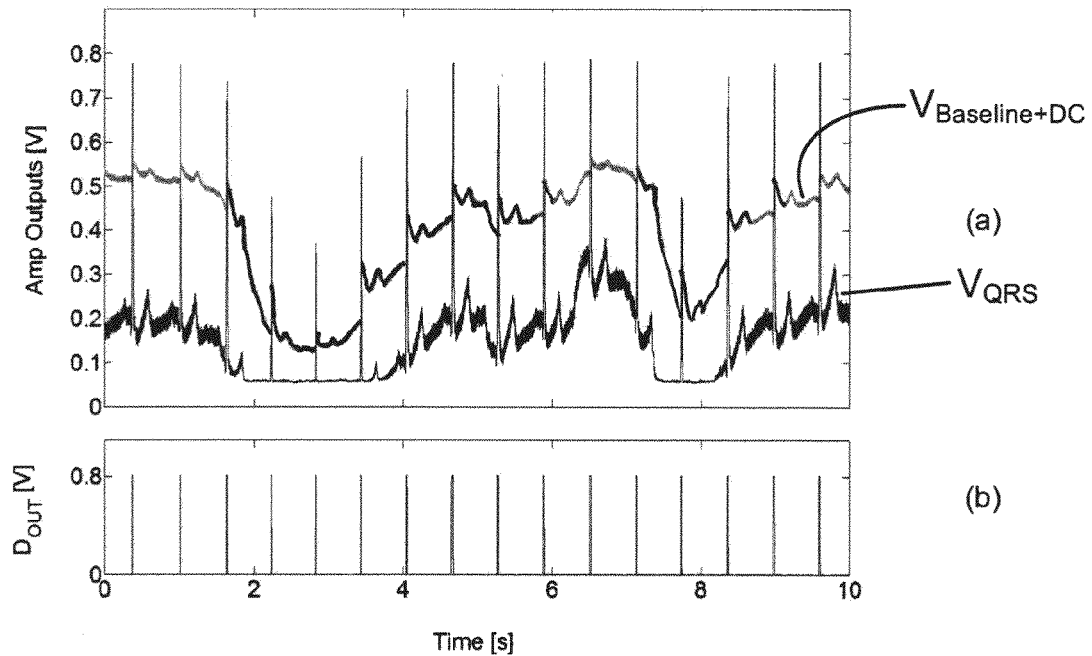
FIG. 13(a) is a chest ECG with baseline drift due to motion of the subject (gain=52 dB)
FIG. 13(b) is the output signal of the device of FIG. 3 of the ECG of FIG. 13(a)
Figure 14:
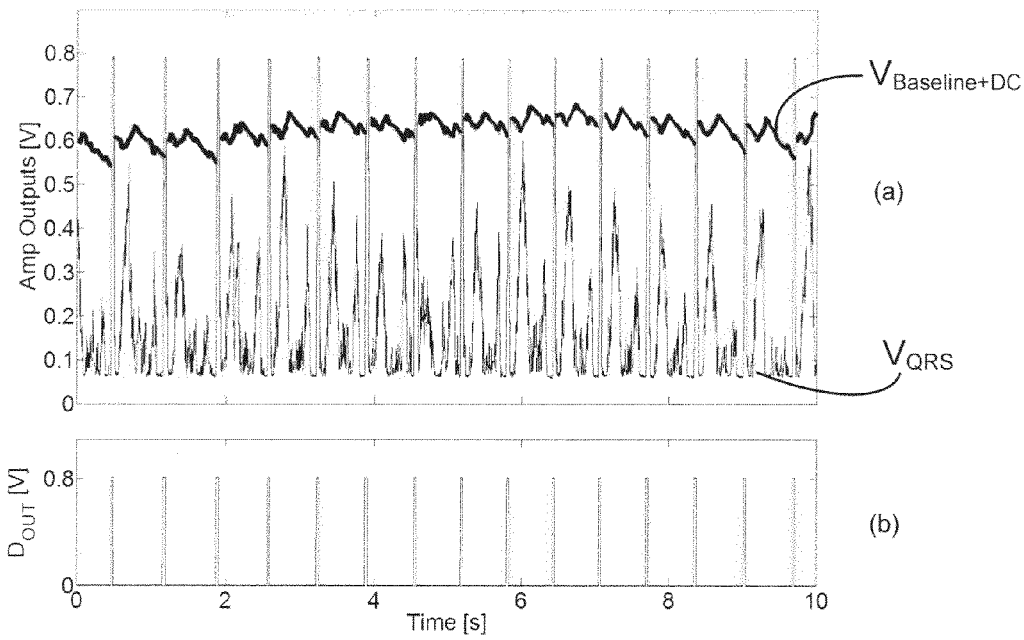
FIG. 14(a) is a chest ECG with muscle artifacts and signal clipping (gain=64 dB)
FIG. 14(b) is the output signal of the device of FIG. 3 of the ECG of FIG. 14(a)
Figure 15:
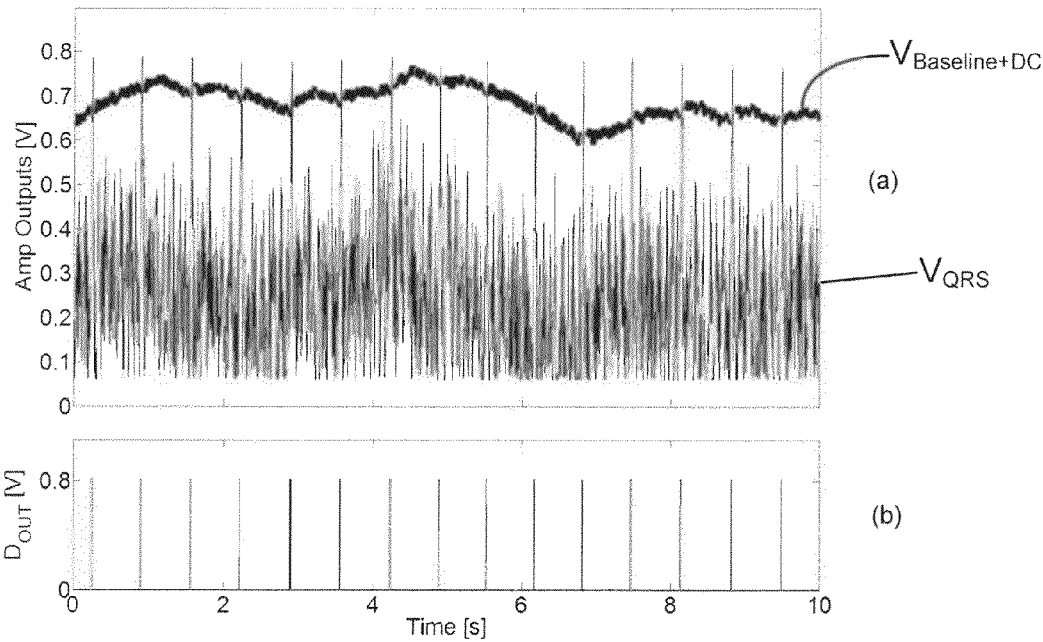
FIG. 15(a) is an ear-neck ECG with high gain and low SNR (gain=84 dB)
FIG. 15(b) is the output signal of the device of FIG. 3 of the ECG of FIG. 15(a)
Figure 16:
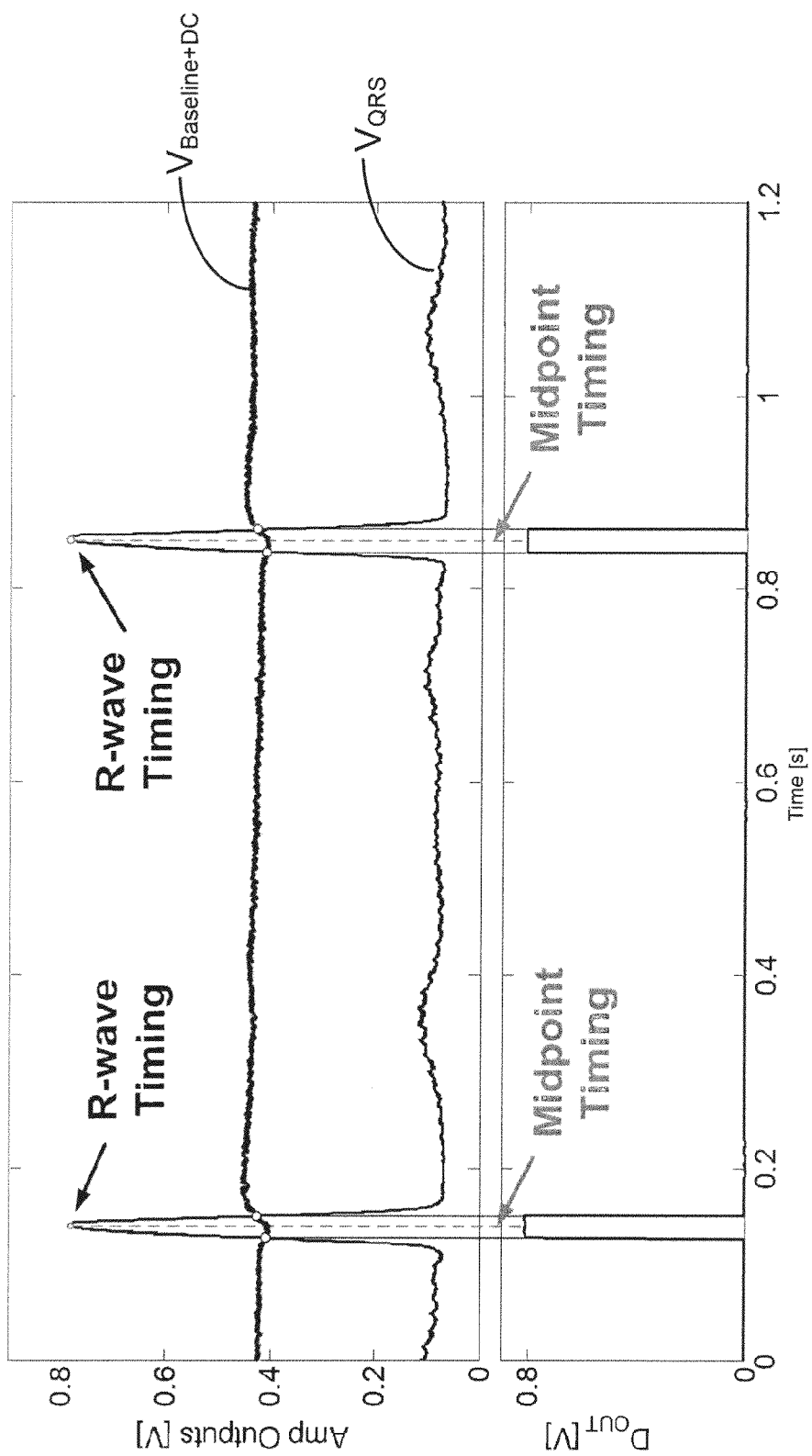
FIG. 16 is a graph indicating how R-wave-timing may be estimated from midpoint timing measurements.

FIGS. 12(a) to 15(b) show measured ECG and digital outputs from various wearable ECG scenarios to demonstrate the ASIC's robustness in the presence of baseline drift, muscle artifacts, and attenuated signal. In FIG. 12(a), the at-rest chest ECG signal offers 1.8 $mV_{pp}$ of stable signal. Here, $V_{DC}$ is set to 0.3V so that $V_{Baseline+DC}$ is approximately half of the $V_{QRS}$ amplitude. However, any $V_{DC}$ setting between 0.1 V and 0.65V would produce the correct digital QRS output at $D_{OUT}$ shown in FIG. 12(b). In FIG. 13(a), the chest ECG contains significant baseline drift due to patient motion. Despite the baseline drift, the same $V_{DC}$ setting as in FIG. 9(a) results in a correct $D_{OUT}$ (FIG. 13(b)). In fact, any $V_{DC}$ setting between 0.1 V-0.5V would suffice. This demonstrates the ASIC's tolerance to motion artifacts because its adaptive threshold $V_{Baseline+DC}$ tracks the baseline drift.

In FIG. 14(a), pectoral muscle artifacts are present from a rapid horizontal 90° arm movement. Also, the higher gain of 64 dB increases the amplified ECG to 2.8$V_{pp}$, which is beyond $V_{DD}$=0.8V and is clipped. To produce the correct $D_{OUT}$ (FIG. 14(b)), $V_{DC}$ needs to be increased to 0.5V so that $V_{Baseline+DC}$ rises above $V_{QRS}$'s muscle artifacts and heightened T-waves. The QRS complex's clipping does not matter because the beat information is still present.

In FIG. 15(a), the ECG is measured across the ear and the middle-upper neck. The gain is increased to 84 dB to sense the 30 p$V_{pp}$ of ear ECG. At this high gain, a significant portion of the amplified output is noise and QRS clipping is present. However, with the identical $V_{DC}$ setting as in FIGS. 12 and 13, $V_{Baseline+DC}$ is able to rise above the noise and allow the correct capture of QRS complexes as shown by $D_{OUT}$ (FIG. 15(b)).

Accurate ECG R-wave timing is necessary for calculations of pre-ejection period (PEP) and pulse arrival time (PAT) for cuffless blood pressure estimation and for calculations of RR intervals for heart rate variability (HRV) analysis. Although the R-wave is clipped and its peak is lost in the eventual digital output $D_{OUT}$, this section shows that the original R-wave timing can be recovered with minimal error.

R-wave timing can be estimated from the midpoint timing of $D_{OUT}$ pulses. This method was tested on normal chest ECG records from ten subjects totaling 2,304 heartbeats. Subjects 1 to 5 were from the MIT-BIR PhysioNet database, and Subjects 6 to 10 were from a MIT clinical test. Estimated R-wave timings are compared with manually annotated timings. The results for all ten subjects are summarized and illustrated in a table 110 shown in FIG. 17.

The mean R-wave timing error arises from the fact that the QR slope may be different from the RS slope, thus resulting in the R-wave not being exactly at the midpoint. The mean R-wave timing error for nine out of ten of the subjects is within the sampling period (4 ms and 2 ms). In six out of ten subjects, the estimation is accurate to within 1 ms of the actual R-wave timing. The standard deviation of R-wave timing error is mainly due to time quantization caused by sampling. As expected, when the sampling frequency is doubled for subjects 6 to 10, the standard deviation of R-wave timing error approximately halves. In nine out of ten subjects, the standard deviation of R-wave timing error is less than half of the sampling period. In summary, the R-wave midpoint estimation method is an accurate way to recover the ECG peak timing information from $D_{OUT}$. This enables the use of the ECG ASIC for applications beyond heartbeat detection, such as cuffless blood pressure estimation and HRV analysis, both of which require accurate R-wave timings.

It should be noted that this circuit, although presented for ECG sensing, can also be applied to other physiological signals that are pulsatile in shape and are synchronous with periodic physiological functions. Such an application of the circuit can extract periodic events such as heartbeat or respiration using non-ECG signals such as PPG, BCG, and respiration.

Some portions of the detailed description are presented in terms of algorithms and symbolic representations of operations on data bits within a computer memory. These algorithmic descriptions and representations can be used by those skilled in the computer and software related fields.

Unless specifically stated otherwise as apparent from the following discussion, it is appreciated that throughout the description, discussions utilizing terms such as "processing" or "computing" or "calculating" or "comparing", "generating" or "determining" or "committing" or "checkpointing" or "interrupting" or "handling" or "receiving" or "buffering" or "allocating" or "displaying" or "flagging" or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

It should be understood that the order of steps or order for performing certain actions is immaterial so long as the present teachings remain operable. Moreover, two or more steps or actions may be conducted simultaneously.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A detection device for amplifying and detecting a periodic signal for storage, transmission, display or processing, the detection device comprising:
a preamplifier cell having a plurality of input terminals and an output terminal, the preamplifier cell amplifying the periodic signal presented at one or more of its input terminals to form a first amplified periodic signal;
a signal amplifier cell having an input terminal and an output terminal, the input terminal of the signal amplifier cell in communication with the output terminal of the preamplifier cell, the signal amplifier cell amplifying the first amplified periodic signal presented at its input terminal, the signal amplifier having a bandwidth sufficient to form a filtered amplified periodic signal preserving the highest frequency pulsatile periodic features of the first amplified periodic signal;
a baseline amplifier cell having an input terminal and an output terminal, the input terminal of the baseline amplifier cell in communication with the output terminal of the preamplifier cell, the baseline amplifier amplifying the first amplified periodic signal presented at its input terminal and having a bandwidth sufficient to form a baseline signal that preserves a baseline voltage while removing the periodic features of the first amplified periodic signal;
a comparator cell having a first input terminal and a second input terminal and an output terminal, the first input terminal of the comparator cell in communication with the output terminal of the signal amplifier cell; and
a $V_{DC}$ cell having a first terminal in communication with the output terminal of the baseline amplifier cell and an output terminal in communication with the second input terminal of the comparator cell, the $V_{DC}$ cell adding a DC offset to the baseline signal to form an offset baseline signal at its output terminal,
wherein the comparator cell generates an output signal in response to the filtered amplified periodic signal from the signal amplifier cell and the offset baseline signal from the $V_{DC}$ cell, the comparator cell output signal comprising a plurality of pulses corresponding to peaks in the periodic signal.

2. The detection device of claim 1, wherein the signal at the input of the preamplifier cell is one of a PPG, a BCG and a respiration signal.

3. The detection device of claim 1, wherein the signal amplifier cell is a QRS amplifier cell.

4. The detection device of claim 1,
wherein the $V_{DC}$ cell has a second input terminal, and
wherein the device further comprises;
a microcontroller cell having an input terminal in communication with the output terminal of the comparator cell and an output terminal in communication with the second input terminal of the $V_{DC}$ cell.

5. The detection device of claim 1, wherein the preamplifier cell is a PGA amplifier.

6. A method for amplifying and detecting a periodic physiological signal comprising the steps of:
amplifying a signal from a physiological signal source using a first amplifier to form a first amplified signal;
amplifying the first amplified signal with a second amplifier having a bandwidth sufficient to form a filtered first amplified signal preserving the with highest frequency pulsatile periodic features of the first amplified signal;
amplifying the first amplified signal with a third amplifier having a bandwidth sufficient to form a baseline signal that preserves a baseline voltage while removing the periodic features of the physiological signal;
adding a DC offset to the baseline signal to form an offset baseline signal using an adder;
comparing the filtered amplified signal to the offset baseline signal using a comparator; and
generating an output signal if the filtered amplified signal is greater than the offset baseline, the output signal comprising a plurality of pulses corresponding to peaks in the periodic physiological signal for storage, transmission, display or processing.

7. The method of claim 6, wherein the bandwidth of the third amplifier is 1 Hz.

8. The method of claim 6, wherein the bandwidth of the third amplifier is 0.05 Hz.

9. The method of claim 6, further comprising adjusting the amplification value of the preamplifier of the signal from the physiological signal source.

10. The method of claim 6, wherein the timing of an R-wave in the QRS signal is estimated in response to measuring the midpoint timing of the corresponding output pulse signal.

11. The method of claim 6, wherein the signal source is an ECG sensor, and the first amplified signal is an amplified ECG signal.

12. The method of claim 11, wherein the amplified ECG signal is amplified by the third amplifier having a bandwidth of 1 Hz to generate the baseline signal.

13. The method of claim 11, wherein the amplified ECG signal is amplified by the second amplifier having a bandwidth of 20-40 Hz to form a QRS signal.

14. The method of claim 13, further comprising selecting the offset baseline comprising the steps of:
a. determining the peak voltage of an R-wave of the QRS signal;
b. determining a baseline DC offset; and
c. calculating one half the difference between the baseline DC offset and peak voltage of the R-wave and adding the baseline DC offset to obtain the offset baseline.

15. The method of claim 13, wherein the QRS signal is compared to the baseline signal offset by a DC offset to form an offset baseline signal.

16. The method of claim 15, further comprising selecting the DC offset comprising the steps of:
a. setting the DC offset to a predetermined value;
b. comparing the filtered amplified ECG signal to the sum of the baseline signal and the DC offset to produce the output signal;
c. if the output signal is not a series of regularly spaced pulses of 40 ppm to 180 ppm then incrementing the DC offset;
d. iteratively repeating steps b and c until the output signal is a series of regularly spaced pulses of 40 ppm to 180 ppm; and
e. setting the DC offset at the value of the DC offset that produces the regularly spaced output signal pulses of 40 ppm to 180 ppm.

* * * * *